(12) United States Patent
Iizuka et al.

(10) Patent No.: US 6,458,971 B1
(45) Date of Patent: Oct. 1, 2002

(54) PROCESS FOR THE PRODUCTION OF MALEIC ANHYDRIDE

(75) Inventors: Yoshiaki Iizuka, Kanagawa; Tatsuya Ihara, Okayama; Yasuyuki Yamauchi, Kanagawa; Mamoru Sawano; Itaru Sawaki, both of Okayama, all of (JP)

(73) Assignee: Mitsubishi Chemical Coporation, Tokyo (JP)

( * ) Notice: Subject to any disclaimer, the term of this patent is extended or adjusted under 35 U.S.C. 154(b) by 0 days.

(21) Appl. No.: 09/577,157

(22) Filed: May 24, 2000

(30) Foreign Application Priority Data

May 25, 1999 (JP) .............................................. 11-144628

(51) Int. Cl.[7] .............................................. C07D 307/60
(52) U.S. Cl. ...................................... 549/259; 549/258
(58) Field of Search .................................. 549/259, 258

(56) References Cited

U.S. PATENT DOCUMENTS

| | | | |
|---|---|---|---|
| 3,904,652 A | | 9/1975 | Frank .......................... 549/250 |
| 4,288,372 A | * | 9/1981 | Hutchings et al. ........... 549/259 |
| 4,317,777 A | * | 3/1982 | Higgins et al. .............. 549/259 |
| 4,987,239 A | | 1/1991 | Ramachandran et al. ... 549/259 |

FOREIGN PATENT DOCUMENTS

| | | |
|---|---|---|
| EP | 0 099 431 | 2/1984 |
| EP | 0 484 136 | 5/1992 |
| EP | 0 486 286 | 5/1992 |
| EP | 0 501 757 | 9/1992 |
| EP | 1 004 567 | 5/2000 |
| JP | 8-9606 | 1/1996 |
| JP | 8-245610 | 9/1996 |
| WO | WO 99/67194 | 12/1999 |

* cited by examiner

*Primary Examiner*—Bernard Dentz
(74) *Attorney, Agent, or Firm*—Oblon, Spivak, McClelland, Maier & Neustadt, P.C.

(57) ABSTRACT

Disclosed is a process for the preparation of maleic anhydride which comprises subjecting an aliphatic hydrocarbon having four or more carbon atoms to gas phase oxidation reaction in the presence of a catalyst, wherein supposing that the function of reaction product gas composition is $F_L$ and the function of temperature and pressure of reaction product gas is $F_R$, the safety index F satisfies the following relationship (1):

$$F = F_L - F_R > 0 \qquad (1)$$

According to the present invention, it is possible that the loss of unreacted hydrocarbon and maleic anhydride as reaction product due to non-catalytic oxidation reaction is prevented while effecting the reaction in a stable manner, whereby the yield of maleic anhydride can be kept maximum while assuring safety.

7 Claims, No Drawings

PROCESS FOR THE PRODUCTION OF MALEIC ANHYDRIDE

FIELD OF THE INVENTION

The present invention relates to a process for the production of maleic anhydride. More particularly, the present invention relates to a process for the production of maleic anhydride which comprises subjecting an aliphatic hydrocarbon having four or more carbon atoms as a raw material to gas phase oxidation reaction in the presence of a catalyst to produce maleic anhydride efficiently in assured safety.

BACKGROUND OF THE INVENTION

In a process for the production of maleic anhydride which comprises subjecting a hydrocarbon as a raw material to gas phase oxidation reaction in the presence of a catalyst in a fluidized bed reactor, a gaseous raw material hydrocarbon previously mixed with an oxygen-containing gas such as air is introduced into a catalyst fluidized bed, or a gaseous raw material hydrocarbon is introduced into a catalyst fluidized bed which has become fluidization by an oxygen-containing gas such as air, thereby causing catalytic reaction. During this procedure, the catalyst is carried above the fluidized bed while being entrained by the reaction product gas. Thus, a dense-phase fluidized bed in which the majority of the catalyst exists is formed and a dilute-phase fluidized bed (freeboard) having a low catalyst density is formed above the dense-phase fluidized bed in the fluidized bed reactor.

In a process for the production of maleic anhydride which comprises subjecting an aliphatic hydrocarbon having four or more carbon atoms to gas phase oxidation reaction in the presence of a catalyst in a fluidized bed reactor, it is usual for the purpose of enhancing the productivity to keep the hydrocarbon concentration in the reactor feed gas higher than that of the reaction using a fixed bed reactor, that is, to supply a hydrocarbon and air as raw material with the concentration of the hydrocarbon, i.e., raw material hydrocarbon in all the feed gases to the reactor being predetermined to a range of from not less than 3.7 vol % to not more than 7.0 vol %. In this case, since the concentration of flammable components in the reaction product gas (sum of the concentration of hydrocarbon, maleic anhydride and carbon monoxide) exceeds so-called lower flammability limit, it is likely that the reaction product gas can further undergo non-catalytic oxidation reaction.

In the reaction using a fluidized bed reactor, this non-catalytic oxidation reaction can be inhibited by the presence of catalyst particles. However, since the dilute-phase fluidized bed has a low catalyst density, it is very likely that the non-catalytic oxidation reaction of maleic anhydride which is a reaction product and the hydrocarbon which is a raw material can proceed. In other words, in an oxygen-containing gas atmosphere such as high temperature air, maleic anhydride and unreacted raw material hydrocarbons which are contained in the reaction product gas in a substantial concentration are liable to non-catalytic oxidation that causes the drop of yield of maleic anhydride as a product. In some cases, abnormal heat generation causes runaway reaction. In extreme cases, explosion can occur.

In order to prevent non-catalytic oxidation reaction in a dilute-phase fluidized bed when the concentration of flammable components in the reaction product gas exceeds the lower flammability limit, a method may be used which comprises keeping the oxygen concentration lower than the minimum oxygen concentration or keeping the flammable component concentration higher than the upper flammability limit.

As a means for inhibiting non-catalytic oxidation there is proposed in JP-B-8-9606 (The term "JP-B" as used herein means an "examined Japanese patent publication") a method which comprises cooling the reaction product gas to a temperature of from 330° C. to 450° C., preferably from 350° C. to 400° C., by means of an indirect heat exchanger provided in the dilute-phase fluidized bed. However, excessive cooling rather raises the possibility of suppression of reaction or deterioration of catalyst. Further, the studies made by the present inventors show that a stable and safe operation is not always sufficient.

The method which comprises reducing the oxygen concentration at the outlet of the reactor to not more than the minimum oxygen concentration of a flammable component having the smallest minimum oxygen concentration among those contained in the reaction product gas, e.g., carbon monoxide, is disadvantageous in that the concentration of oxygen in the reaction product gas is excessively lowered, resulting in an undesirable drop of yield of maleic anhydride, and the resulting low oxygen concentration atmosphere causes excessive reduction that deteriorates the catalyst.

On the other hand, no method for accurately estimating the upper flammability limit of the reaction product gas has been known, making it impossible to employ a method which comprises keeping the flammable component concentration higher than the upper flammability limit in a relatively high oxygen concentration range.

While in the case of a reaction executed in a fixed bed reactor, since the concentration of flammable components in the reaction product gas is normally lower than the lower flammability limit, there does not cause such problems. However, methods of increasing the raw materials concentration or recycling the unreacted hydrocarbon are proposed recently in order to enhance the productivity, there is a possibility of causing non-catalytic oxidation even in the case of the fixed bed reactor.

SUMMARY OF THE INVENTION

The present invention has been worked out on the basis of the conventional techniques for the purpose of providing a process for the production of maleic anhydride which comprises subjecting an aliphatic hydrocarbon having four or more carbon atoms to gas phase oxidation reaction in the presence of a catalyst, characterized in that the loss of unreacted hydrocarbon and maleic anhydride as reaction product due to non-catalytic oxidation of the reaction product gas is prevented, the yield of maleic anhydride is kept high as much as possible while assuring safety, and the reduction deterioration of the catalyst is prevented, making it possible to produce maleic anhydride in safety and in an economical manner. In other words, the provision of a means for confirming that the reaction product gas always lies in a flammable component concentration range above the upper flammability limit allows economic operation with assured safety.

The inventors made extensive studies of the foregoing problems. As a result, it was found that when the temperature, the pressure and the composition of the reaction product gas satisfy the predetermined relationships, no oxidation reaction takes place even in the absence of catalyst, making it possible to produce maleic anhydride efficiently in safety. Thus, the present invention has been worked out.

The present invention provides a process for the preparation of maleic anhydride which comprises subjecting an aliphatic hydrocarbon having four or more carbon atoms to gas phase oxidation reaction in the presence of a catalyst, wherein supposing that the function of reaction product gas composition is $F_L$ and the function of temperature and pressure of reaction product gas is $F_R$, the safety index F satisfies the following relationship (1)

$$F=F_L-F_R>0 \tag{1}$$

wherein $F_L$ represents the value calculated by the following equation (2):

$$F_L=C/C_T/C_O \tag{2}$$

wherein

C represents the concentration (vol %) of flammable gas in the reaction product gas;

$C_O$ represents the concentration (vol %) of oxygen gas in the atmosphere; and $C_T$ represents the stoichiometric flammable gas concentration (vol %): and $F_R$ represents the value calculated by the following equation (3):

$$F_R=2.319\times10^{-5}\times T^2-1.688\times10^{-2}\times T+3.288+(P-0.15)\times0.3 \tag{3}$$

wherein

T represents the temperature (°C.) of reaction product gas; and

P represents the reaction pressure (MPaG).

In accordance with another embodiment of implication of the present invention, a process for the preparation of maleic anhydride is provided which comprises subjecting an aliphatic hydrocarbon having four or more carbon atoms to gas phase oxidation reaction in the presence of a catalyst in a fluidized bed reactor, wherein the feed flow rate of oxygen-containing gas, the feed flow rate of hydrocarbon, the reaction temperature, the temperature of reaction product gas, the reaction pressure or the amount of catalyst is adjusted such that supposing that the function of reaction product gas composition is $F_L$ and the function of temperature and pressure of reaction product gas is $F_R$, the safety index F satisfies the following relationship (1):

$$F=F_L-F_R>0 \tag{1}$$

wherein $F_L$ represents the value calculated by the following equation (2):

$$F_L=C/C_T/C_O \tag{2}$$

wherein

C represents the concentration (vol %) of flammable gas in the reaction product gas;

$C_O$ represents the concentration (vol %) of oxygen gas in the atmosphere; and $C_T$ represents the stoichiometric flammable gas concentration (vol %); and $F_R$ represents the value calculated by the following equation (3):

$$F_R=2.319\times10^{-5}\times T^2-1.688\times10^{-2}\times T+3.288+(P-0.15)\times0.3 \tag{3}$$

wherein

T represents the temperature (°C.) of reaction product gas; and

P represents the reaction pressure (MPaG).

DETAILED DESCRIPTION OF THE INVENTION

In the process according to the present invention, a hydrocarbon as a raw material and an oxygen-containing gas are allowed to come in contact with each other in a reactor containing an oxidation catalyst to undergo gas phase oxidation reaction, thereby producing maleic anhydride.

The oxidation catalyst to be used in the present invention is not specifically limited so far as it is a catalyst useful for the production of maleic anhydride. In practice, however, a catalyst comprising a vanadium-phosphorus mixed oxide as a main component is particularly preferred. As such a catalyst there may be used an oxidation catalyst comprising as an active component a mixed oxide comprising vanadium and phosphorus as main constituents. Examples of such an oxidation catalyst employable herein include those produced by conventional known methods described in U.S. Pat. Nos. 4,525,471, 4,317,778, 4,511,670, 4,520,127, 5,530,144, and 5,498,731.

The properties of the catalyst to be used in a fluidized bed reactor in the present invention may be that of the catalyst for use in ordinary fluidized bed reactors. The catalyst of the invention preferably belongs to Geldert's particle classification map A (see Geldert D., *Powder Technology*, 7, 285 (1973)), i.e., has a mass mean particle diameter of preferably from 30 to 100 μm, more preferably from 40 to 80 μm, comprises a fine powder having a particle diameter of 44 μm or less in an amount of from 10 to 80% by weight, more preferably from 20 to 70% by weight has a particle density of 5,000 kg/m³ or less, more preferably 4,000 kg/m³ or less.

When the catalyst has a mass mean particle diameter of less than 30 μm or comprises a fine powder having a particle diameter of 44 μm or less in an amount of more than 80% by weight, the amount of the catalyst entrained from the fluidized bed reactor increases, deteriorating economy. When the catalyst has a mass mean particle diameter of more than 100 μm, comprises a fine powder having a particle diameter of 44 μm or less in an amount of less than 10% by weight or has a particle density of more than 5,000 kg/m³, the resulting particle has too heavy and thus is not suitable for the use in the fluidized bed reactor where particles are fluidized to undergo gas-solid contact.

As the hydrocarbon to be used as a raw material there may be used an aliphatic hydrocarbon having four or more carbon atoms. Preferred examples of such an aliphatic hydrocarbon include butanes such as n-butane, butenes such as 1-butene and 2-butene, and butadienes such as 1,2-butadiene and 1,3-butadiene. Particularly preferred among these aliphatic hydrocarbons is n-butane.

As the oxygen-containing gas there may be normally used air. Alternatively, air diluted with an inert gas or air enriched with oxygen may be used.

The concentration of hydrocarbon to be used as a raw material and oxygen in the gas to be supplied into the reactor are not specifically limited. In the high conversion reaction, which is usually effected, the hydrocarbon concentration is preferably from not less than 3.7 vol % to not more than 7.0 vol %, more preferably not less than 4.0 vol % to not more than 6.0 vol %, and the oxygen concentration is preferably from not less than 18 vol % to not more than 35 vol %, more preferably from not less than 19 vol % to not more than 30 vol %. In the case where the hydrocarbon which has been left unreacted is recovered and returned to the reactor for re-use, the oxygen concentration is preferably adjusted to a range of from not less than 20 vol % to not more than 50 vol %, more preferably not less than 25 vol % to not more than 40 vol %, and the hydrocarbon concentration (vol %) is preferably adjusted such that the volume ratio of oxygen concentration to hydrocarbon concentration is from not less than 1 to not more than 5.

In the case where the reactor is executed in the fluidized bed reactor in the present invention, the fluidized bed reactor preferably comprises a gas distributor plate provided at the bottom of the reactor defining the lower end of the catalyst fluidized bed, an oxygen-containing gas supply pipe, a raw material hydrocarbon supply pipe, and a product gas outlet provided at the top of the reactor. Further, the hydrocarbon supply port is preferably opened at the position upwardly apart from the gas distributor plate. A fine particle collector such as cyclone and catalyst filter for separating entrained catalyst from the reaction product gas may be provided either inside or outside the reactor. The catalyst which has been recovered by the fine particle collector is preferably returned to the lower region of the dense-phase fluidized bed. These devices to be provided in the fluidized bed reactor and their positions may be as known and used ordinarily themselves. Preferably, an indirect heat exchanger for cooling the reaction product gas, e.g., cooling coil is provided at the position where a dense-phase fluidized bed and a dilute-phase fluidized bed should be formed.

The oxidation catalyst on the gas distributor plate in the fluidized bed reactor becomes fluidized by the gas supplied through the gas distributor plate at the bottom of the reactor to form a dense-phase fluidized bed above the gas distributor plate. In the dense-phase fluidized bed, the raw material hydrocarbon undergoes gas phase oxidation reaction to produce maleic anhydride. Thereafter, the reaction product gas containing unreacted raw material hydrocarbon and oxygen, and by-produced carbon dioxide, carbon monoxide and water besides maleic anhydride thus produced flows out of the dense-phase fluidized bed while entraining a small amount of catalyst, thereby forming a dilute-phase fluidized bed thereabove. Subsequently, the reaction product gas is introduced into the fine particle collector such as cyclone provided at the top (inside or outside) of the reactor where it is then separated from the entrained catalyst. The reaction product gas is then withdrawn from the reactor. Maleic anhydride is then recovered from the reaction product gas thus withdrawn.

The separation and recovery of maleic anhydride can be accomplished by any commonly used method known as such, e.g., method which comprises cooling the reaction gas to condense maleic anhydride, method which comprises allowing the reaction gas to come in contact with water to collect maleic anhydride in water as maleic acid, method which comprises allowing the reaction gas to come in contact with an organic solvent such as phthalic acid dialkyl ester or alkyl ester of hydrogenated phthalic acid (e.g., tetrahydrophthalic acid, hexahydrophthalic acid) to collect maleic anhydride in the organic solvent.

As disclosed in JP-A-8-325256, the raw material hydrocarbon which has been left unreacted may be recovered from the gas which has been left behind after the separation and recovery of maleic anhydride from the reaction product gas and then returned to the reactor for re-use. In this case, a fresh oxygen-containing gas and a hydrocarbon are fed into the reactor in such an amount that the concentrations of oxygen and hydrocarbon in all the feed gases are kept at predetermined values.

The temperature of gas phase oxidation reaction in the dense-phase fluidized bed is normally from 330° C. to 500° C., preferably from 380° C. to 500° C., more preferably from 400° C. to 460° C. The pressure P is normally from ordinary pressure to 0.5 MPaG, preferably from 0.05 to 0.3 MPaG.

In the process of the present invention, it is essential that supposing that the function of reaction product gas composition is $F_L$ and the function of temperature and pressure of reaction product gas is $F_R$, the safety index F satisfies the following relationship (1):

$$F = F_L - F_R > 0 \tag{1}$$

wherein $F_L$ represents the value calculated by the following equation (2):

$$F_L = C/C_T/C_O \tag{2}$$

wherein

C represents the concentration (vol %) of flammable gas in the reaction product gas;

$C_O$ represents the oxygen gas concentration (vol %) in the atmosphere; and $C_T$ represents the stoichiometric flammable gas concentration (vol %); and $F_R$ represents the value calculated by the following equation (3):

$$F_R = 2.319 \times 10^{-5} \times T^2 - 1.688 \times 10^{-2} \times T + 3.288 + (P - 0.15) \times 0.3 \tag{3}$$

wherein

T represents the temperature (°C.) of reaction product gas; and

P represents the reaction pressure (MPaG).

The foregoing equations mean that the concentration of flammable component in the reaction product gas is higher than the upper flammability limit. The left side F of the foregoing relationship (1) is a concept representing how much margin the concentration of flammable component in the reaction product gas has with respect to the upper flammability limit. The foregoing relationships (1) to (3) are empirical formulae obtained by the present inventors as a result of a lot of explosion experiments but don't indicate theoretical relationships. However, it is important in the present invention that it was found that when the composition, temperature and pressure of the reaction product gas satisfy the foregoing relationships (1) to (3), the concentration of flammable component in the reaction product gas is kept higher than the upper flammability limit, causing no non-catalytic reaction and hence assuring safety.

In the foregoing relationship (1), the function $F_L$ of the composition of reaction product gas is calculated from the following relationship (2):

$$F_L = C/C_T/C_O \tag{2}$$

In the foregoing relationship (2), C represents the concentration (vol %) of flammable gas in the reaction product gas. Supposing that various flammable gases in the reaction product gas are numbered 1, 2, 3, . . . , i, . . . , n, respectively, and the concentration (vol %) of various flammable gases are C1, C2, C3, . . . , Ci, . . . , Cn, respectively, C can be calculated from the following equation (4):

$$C = \sum_{i=1}^{n} Ci \quad (4)$$

In actuality, the majority of the flammable gas in the reaction product gas is occupied by maleic anhydride, unreacted hydrocarbon and carbon monoxide. Accordingly, the concentration C (vol %) of the flammable gas in the reaction product gas can be obtained from the three components. Thus, it is usually unnecessary to take other components into account.

The oxygen gas concentration $C_O$ (vol %) in the atmosphere means the concentration of oxygen gas in the gas (remaining gas) obtained by removing flammable gas from all the gases, i.e., the concentration of oxygen gas in inert gas and oxygen, which can be calculated from the following equation (5):

$C_O$={Concentration (vol %) of oxygen in the reaction product gas/ $(100-C)$}×100 (5)

In this case, the inert gas is $CO_2$, $H_2O$, Ar, $N_2$ or the like. The idea of oxygen gas concentration in the atmosphere $C_O$ is a concept that is often used when the flammability range of gas is taken into account.

The stoichiometric flammable gas concentration $C_T$ (vol %) means the concentration of flammable component at which flammable gases in the reaction gas can be completely combusted with oxygen contained in the reaction product gas. Supposing that the ratio of the stoichiometric amounts of oxygen to the amounts of each flammable component required for complete combustion are R1, R2, R3, . . . , Ri, . . . , Rn, respectively, $C_T$ can be calculated from the following equation (6):

$$C_T = 100 \Bigg/ \left[ 1 + \left\{ \left( \sum_{i=1}^{n} (RixCi) \Big/ \sum_{i=1}^{n} Ci \right) \Big/ Co \right\} \times 100 \right] \quad (6)$$

In actuality, however, the stoichiometric flammable gas concentration $C_r$ may be calculated taking into account the three components in the reaction product gas, i.e., maleic anhydride, unreacted hydrocarbon and carbon monoxide, as in the flammable gas concentration C. For example, supposing that the molar fraction of maleic anhydride, butane and carbon monoxide occupying all the flammable gases in the reaction product are a, b and c, respectively, while the number of mols of oxygen gas required for the complete combustion of 1 mol of these flammable components are 3 mols, 6.5 mols and 0.5 mol, respectively, $C_T$ can be calculated from the following equation (7):

$C_T$=100/[1+{(3a+6.5b+0.5c)/Co}×100] (7)

$F_L$ calculated from the equation (2) approaches infinity as the oxygen concentration approaches 0 infinitely. $F_L$ becomes 0 as the flammable component concentration becomes 0. Thus, the value of $F_L$ is not specifically limited.

In the equation (1), the function $F_R$ of temperature and pressure can be calculated from the following equation (3):

$F_R$=2.319×10$^{-5}$×$T^2$−1.688×10$^{-2}$×$T$+3.288+($P$−0.15)×0.3 (3)

In the equation (3), T represents the temperature (°C.) of the reaction product gas, and P represents the reaction pressure (MPaG). The temperature T and pressure P may be values determined at points where monitoring are required in the foregoing production process. Since the pressure in the dilute-phase fluidized bed in the fluidized bed reactor is normally almost the same all over the points, the pressure P may be determined at any points. The temperature T differs from one point to another in the reactor for the production of maleic anhydride. The safety in various points can be represented by the foregoing relationships (1) to (3). In the foregoing reactor, the lower the temperature is, the higher is the safety. Even when the temperature is high, the safety can be assured where there is a plenty of catalyst. In other words, the possibility of non-catalytic oxidation reaction becomes highest at positions where there exists little or no catalyst and the temperature is high. Accordingly, by confirming that the most dangerous position during the reaction step is safe according to the relationship (1), the safety all over the reaction step can be assured.

The provision of the foregoing relationships of the invention makes it possible to simply confirm safety according to the temperature of the most dangerous position during the reaction step and the reaction gas composition and hence produce maleic anhydride efficiently in safety. In general, the position in the fine particle collector such as cyclone where the catalyst and the gas are separated from each other is the most dangerous position. Thus, the temperature at the inlet of the fine particle collector or the like may be used as the temperature of reaction product gas.

$F_R$ in the relationship (3) is the function of temperature and pressure. The range of value of $F_R$ is determined by the range of reaction temperature and reaction pressure in the foregoing process for the production of maleic anhydride. From the standpoint of experimental range from which the relationship (3) is derived and the properties of the relationship (3), the effective numerical range of the temperature T of the reaction product gas may be from not lower than 365° C. to not higher than 460° C. The numerical range of the pressure is not specifically limited.

The composition of reaction product gas can be determined by directly analyzing the gas at the position where monitoring is required, such as outlet of the reactor, by gas chromatography or the like. Alternatively, the composition of gas at the outlet of the reactor can be calculated from the analysis of the gas (e.g., gas at the outlet of absorption column) obtained by separating maleic anhydride from the reaction product gas and the composition of the gas to be fed to the reactor.

In the foregoing relationship (1), it is preferred that the function $F_L$ of the reaction product gas composition and the function $F_R$ of temperature and pressure be each calculated to the fourth decimal place which is then rounded to obtain values to the third decimal place from which the safety index is determined.

In the case of $F_L$−$F_R$=0, it indicates the border of flammability and nonflammability. When $F_L$ is equal to or smaller than $F_R$, operation cannot be effected in assured safety. In general, when $F_L$ is greater than $F_R$, i.e., the safety index F is greater than 0, maleic anhydride can be produced in safety. The safety index F is preferably from more than 0 to not more than 15.0, more preferably from more than 0 to not more than 2.0. In particular, when the conversion of raw material hydrocarbon is 70% or more, the safety index F is preferably from more than 0 to not more than 2.0, particularly from 0.1 to 1.0. When the safety index F falls below 0, the possibility of non-catalytic oxidation reaction of the reaction product gas can be raised. Taking into account the errors in the analysis of the reaction product gas and the measurements of temperature or pressure, the safety index is preferably kept at 0.1 or more. On the contrary, when the safety index is excessive, it is likely that the yield of maleic anhydride can decrease or the resulting drop of oxygen concentration can cause the reduction deterioration of the catalyst.

In the case where the raw material which has been left unreacted in the reactor is recovered from the gas obtained by separating and recovering maleic anhydride from the reaction product gas and then returned to the reactor for re-use, the conversion of raw material hydrocarbon (Z %) preferably falls within the range represented by the relationship $20(Y-10)/X \geq Z \geq 25Y/X$, supposing that the concentration (vol %) of raw material hydrocarbon is X and the oxygen concentration (vol %) is Y. Under these production conditions, the safety index F is preferably from more than 0 to not more than 15.0, more preferably from 0.1 to 10.0.

In the operation of the reactor according to the invention, the various parameters of the foregoing relationships (2) to (7) are calculated from the measurements of temperature and pressure at the position where monitoring is needed, e.g., inlet of cyclone in the dilute-phase fluidized bed in the case of using fluidized bed reactor, and the composition of the reaction product gas to determine the safety index F of the relationship (1). Since temperature and pressure can be easily measured at any time, the newest value is preferably used every time.

On the other hand, it is difficult to measure the concentration of all components in the gas composition at the outlet of the reactor all the time. However, the composition of the gas at the outlet of the reactor can be intermittently determined by directly analyzing the composition of the reaction product gas by gas chromatography, or by calculating from the analysis of the composition of gas at the outlet of the absorption column by gas chromatography and the flow rate of the various fluids which are fed to the reactor. The safety index F can be regarded constant until the analysis is renewed. However, the safety index F is preferably calculated every time on the assumption that the results of reaction (e.g., conversion of hydrocarbon and maleic anhydride yield) are constant or the reaction gas composition is constant. Then, the feed flow rate of oxygen-containing gas, the feed flow rate of hydrocarbon, the reaction temperature, the temperature of reaction product gas, the reaction pressure or the amount of catalyst is adjusted during the operation of the reactor such that the safety index F satisfies the foregoing requirements.

When the safty index F obtained by the foregoing relationship (1) is too small, in order to effectively allow the operation of the reactor such that the safety index F satisfies the relationship (1), the reactor can be operated under modified conditions such that $F_L$ in the relationship (1) is raised or $F_R$ in the relationship (1) is reduced. Specific useful examples of the method for raising $F_L$ include a method which comprises reducing the feed flow rate of oxygen-containing gas to the reactor, a method which comprises raising the feed flow rate of hydrocarbon, and a method which comprises raising the reaction temperature or the amount of catalyst to raise the conversion of raw material hydrocarbon. On the other hand, specific useful examples of the method for reducing $F_R$ include a method which comprises lowering the temperature of the dilute-phase fluidized bed region by cooling or like means or lowering the reaction temperature by raising the amount of catalyst, thereby lowering the temperature of the reaction product gas, and a method which comprises lowering the reaction pressure. These operational conditions may be adjusted individually or in combination at the same time. Thus, maleic anhydride can be produced efficiently in safety.

The foregoing description is focused on the case of using fluidized bed reactor. However, even in the case of using fixed bed reactor, when the concentration of the flammable components in the reaction product gas exceeds the lower flammability limit, maleic anhydride can be produced in safety by keeping the concentration of the flammable components always higher than the upper flammability limit according to the present invention.

EXAMPLES

The present invention will be further described in the following examples, but the present invention should not be construed as being limited thereto.

Examples 1 to 7 and Comparative Examples 1 to 11

On the assumption that maleic anhydride is produced from a butane-air mixed gas as a raw material and the composition of the feed gas and the results of reaction are varied, the composition of the gas at the outlet of the reactor was calculated. A makeup gas having the composition thus calculated was prepared. The flammability and nonflammability conditions of the makeup gas were then experimentally determined as follows.

Into a 1 liter capacity pressure explosion vessel in which the air within had been evacuated were introduced maleic anhydride, n-butane, carbon monoxide, air, nitrogen and water in such an amount that the gas composition and pressure set forth in Tables 1 and 2 were reached. A nichrome wire coil (5 turns of nichrome wire) provided at the bottom of the vessel was then energized (11 V×12 A×1 second=130 J) to ignite the mixed gas. The resulting change in the inner pressure of the vessel was then measured to judge if the gas was exploded.

The results are set forth in Tables 1 and 2. In the tables, "results of reaction" are represented as estimated value, and "gas composition" is the composition of makeup gas which corresponds to the composition of the gas at the outlet of the reactor calculated from the results of reaction.

TABLE 1

|  | Comparative Example 1 | Comparative Example 2 | Example 1 | Comparative Example 3 | Comparative Example 4 | Example 2 | Comparative Example 5 | Comparative Example 6 | Example 3 |
|---|---|---|---|---|---|---|---|---|---|
| Gas composition (vol %) | | | | | | | | | |
| * Maleic anhydride | 1.73 | 1.75 | 1.77 | 1.79 | 1.81 | 1.83 | 1.77 | 1.80 | 1.82 |
| * n-Butane | 0.72 | 0.73 | 0.74 | 0.43 | 0.44 | 0.44 | 0.74 | 0.75 | 0.76 |
| * Carbon monoxide | 2.80 | 2.83 | 2.86 | 3.09 | 3.12 | 3.16 | 2.86 | 2.89 | 2.93 |
| * Oxygen | 6.73 | 6.56 | 6.39 | 5.84 | 5.66 | 5.48 | 6.39 | 6.22 | 6.05 |
| * Water | 16.70 | 16.88 | 17.06 | 17.71 | 17.91 | 18.10 | 17.06 | 17.23 | 17.40 |

TABLE 1-continued

| | Comparative Example 1 | Comparative Example 2 | Example 1 | Comparative Example 3 | Comparative Example 4 | Example 2 | Comparative Example 5 | Comparative Example 6 | Example 3 |
|---|---|---|---|---|---|---|---|---|---|
| * Nitrogen | 71.32 | 71.25 | 71.18 | 71.14 | 71.06 | 70.99 | 71.18 | 71.11 | 71.04 |
| Temperature (° C.) | 400 | 400 | 400 | 420 | 420 | 420 | 420 | 420 | 420 |
| Pressure (MPaG) | 0.15 | 0.15 | 0.15 | 0.15 | 0.15 | 0.15 | 0.15 | 0.15 | 0.15 |
| Flammable gas concentration: C (vol %) | 5.25 | 5.31 | 5.37 | 5.31 | 5.37 | 5.43 | 5.37 | 5.44 | 5.51 |
| Oxygen gas concentration: $C_O$ (vol %) | 7.10 | 6.93 | 6.75 | 6.17 | 5.98 | 5.79 | 6.75 | 6.58 | 6.40 |
| Stiochiometric flammable gas concentration: $C_T$ (vol %) | 3.20 | 3.12 | 3.04 | 3.26 | 3.16 | 3.07 | 3.04 | 2.96 | 2.89 |
| $F_L$ in relationship (1) | 0.231 | 0.245 | 0.261 | 0.264 | 0.284 | 0.305 | 0.261 | 0.279 | 0.298 |
| $F_R$ in relationship (1) | 0.246 | 0.246 | 0.246 | 0.289 | 0.289 | 0.289 | 0.289 | 0.289 | 0.289 |
| $F_L - F_R$ | −0.015 | −0.001 | 0.015 | −0.025 | −0.005 | 0.016 | −0.028 | −0.010 | 0.009 |
| Result of ignition | Exploded | Exploded | Not exploded | Exploded | Exploded | Not exploded | Exploded | Exploded | Not exploded |
| Assumed composition of feed to reactor and results of reaction | | | | | | | | | |
| * n-Butane concentration (vol %) | 3.75 | 3.80 | 3.85 | 3.64 | 3.69 | 3.74 | 3.85 | 3.90 | 4.00 |
| * n-Butane conversion (%) | 80.0 | 80.0 | 80.0 | 87.7 | 87.7 | 87.7 | 80.0 | 80.0 | 80.0 |
| * Yield of maleic anhydride (%) | 48.0 | 48.0 | 48.0 | 51.2 | 51.2 | 51.2 | 48.0 | 48.0 | 48.0 |
| * $co/co_2$ ratio | 1.530 | 1.530 | 1.530 | 1.532 | 1.532 | 1.532 | 1.532 | 1.532 | 1.532 |

TABLE 2

| | Comparative Example 7 | Example 4 | Example 5 | Comparative Example 8 | Example 6 | Comparative Example 9 | Example 7 | Comparative Example 10 | Comparative Example 11 |
|---|---|---|---|---|---|---|---|---|---|
| Gas composition (vol %) | | | | | | | | | |
| * Maleic anhydride | 2.16 | 2.18 | 2.21 | 1.97 | 2.99 | 1.95 | 1.99 | 2.00 | 2.04 |
| * n-Butane | 0.77 | 0.78 | 0.79 | 0.57 | 0.57 | 0.57 | 0.58 | 0.77 | 0.79 |
| * Carbon monoxide | 2.24 | 2.27 | 2.29 | 2.72 | 2.70 | 2.66 | 2.83 | 2.60 | 2.66 |
| * Oxygen | 6.48 | 6.32 | 6.16 | 5.63 | 5.42 | 5.54 | 5.22 | 6.18 | 5.85 |
| * Water | 16.90 | 17.08 | 17.25 | 16.38 | 16.64 | 16.54 | 16.83 | 17.25 | 17.59 |
| * Nitrogen | 71.45 | 71.37 | 71.30 | 72.73 | 72.68 | 72.74 | 72.55 | 71.20 | 71.07 |
| Temperature (° C.) | 420 | 420 | 420 | 450 | 450 | 450 | 450 | 450 | 450 |
| Pressure (MPaG) | 0.15 | 0.15 | 0.15 | 0.0 | 0.0 | 0.10 | 0.10 | 0.15 | 0.15 |
| Flammable gas concentration: C (vol %) | 5.17 | 5.23 | 5.29 | 5.26 | 5.26 | 5.18 | 5.40 | 5.37 | 5.49 |
| Oxygen gas concentration: $C_O$ (vol %) | 6.83 | 6.67 | 6.50 | 5.94 | 5.72 | 5.84 | 5.52 | 6.53 | 6.19 |
| Stiochiometric flammable gas concentration: $C_T$ (vol %) | 2.73 | 2.66 | 2.60 | 2.77 | 2.66 | 2.71 | 2.60 | 2.77 | 2.63 |
| $F_L$ in relationship (1) | 0.278 | 0.294 | 0.313 | 0.320 | 0.346 | 0.328 | 0.376 | 0.297 | 0.337 |
| $F_R$ in relationship (1) | 0.289 | 0.289 | 0.289 | 0.343 | 0.343 | 0.373 | 0.373 | 0.388 | 0.388 |
| $F_L - F_R$ | −0.011 | 0.005 | 0.024 | −0.023 | 0.003 | −0.045 | 0.003 | −0.091 | −0.051 |
| Result of ignition | Exploded | Not exploded | Not exploded | Exploded | Not exploded | Exploded | Not exploded | Exploded | Exploded |
| Assumed composition of feed to reactor and results of reaction | | | | | | | | | |
| * n-Butane concentration (vol %) | 4.00 | 4.05 | 4.10 | 3.90 | 4.00 | 3.95 | 4.05 | 4.00 | 4.10 |
| * n-Butane conversion (%) | 80.0 | 80.0 | 80.0 | 85.0 | 85.0 | 85.0 | 85.0 | 80.0 | 80.0 |
| * Yield of maleic anhydride (%) | 56.0 | 56.0 | 56.0 | 52.0 | 52.0 | 51.5 | 51.5 | 52.0 | 52.0 |
| * $co/co_2$ ratio | 1.532 | 1.532 | 1.532 | 1.200 | 1.150 | 1.100 | 1.200 | 1.532 | 1.532 |

The present invention provides an efficient process for the production of maleic anhydride which comprises subjecting an aliphatic hydrocarbon having four or more carbon atoms to gas phase oxidation reaction in the presence of a catalyst, wherein the loss of unreacted hydrocarbon and maleic anhydride as reaction product due to non-catalytic oxidation reaction is prevented while effecting the reaction in a stable manner, whereby the yield of maleic anhydride can be kept maximum while assuring safety.

While the invention has been described in detail and with reference to specific embodiments thereof, it will be apparent to one skilled in the art that various changes and modifications can be made therein without departing from the spirit and scope thereof.

This application is based on Japanese patent application Hei-11-144628, filed on May 25, 1999, incorporated herein by reference.

What is claimed is:

1. A process for the preparation of maleic anhydride which comprises subjecting an aliphatic hydrocarbon having four or more carbon atoms to gas phase oxidation reaction in the presence of a catalyst, wherein supposing that the function of reaction product gas composition is $F_L$ and the function of temperature and pressure of reaction product gas is $F_R$, the safety index F satisfies the following relationship (1):

$$F=F_L-F_R>0 \tag{1}$$

wherein $F_L$ represents the value calculated by the following equation (2):

$$F_L=C/C_T/C_O \tag{2}$$

wherein

C represents the concentration (vol %) of flammable gas in the reaction product gas, supposing that various flammable gases in the reaction product gas are numbered, 1, 2, 3, . . . , i, . . . n, respectively, and the concentration (vol %) of various flammable gases are C1, C2, C3, . . . , Ci, . . . , Cn, respectively, C can be calculated from the equation $$C = \sum_{i=1}^{n} Ci;$$

$C_O$ represents the oxygen gas concentration (vol %) in the atmosphere meaning the concentration of oxygen gas in the gas obtained by removing flammable gas from all the gases, which can be calculated from the equation $C_o$={Concentration (vol %) of oxygen in the reaction product gas/(100-$C$)}×100;

and $C_T$ represents the stoichiometric flammable gas concentration (vol %) meaning the concentration of flammable component at which flammable gases in the reaction gas can be completely combusted with oxygen contained in the reaction product gas, supposing that the ratio of the stoichiometric amounts of oxygen to the amounts of each flammable component required for complete combustion are R1, R2, R3, . . . Ri, . . . , Rn, respectively, $C_T$ can be calculated from the following equation:

$$C_T = 100 \Big/ \left[1 + \left\{\left(\sum_{i=1}^{n}(RixCi)\Big/\sum_{i=1}^{n}Ci\right)\Big/Co\right\} \times 100\right]$$

and $F_R$ represents the value calculated by the following equation (3)

$$F_R=2.319\times10^{-5}\times T^2-1.688\times10^{-2}T+3.288+(P-0.15)\times0.3 \tag{3}$$

wherein

T represents the temperature (°C.) of reaction product gas; and P represents the reaction pressure (MPaG).

2. The process according to claim 1, wherein 0<F≦15.0.

3. The process according to claim 1, wherein 0<F≦2.0.

4. The process according to any one of claims 1 to 3, wherein said catalyst is a vanadium-phosphorus mixed oxide catalyst.

5. The process according to any one of claims 1 to 3, wherein said gas phase oxidation reaction is executed in a fluidized bed reactor.

6. The process according to any one of claims 1 to 3, wherein said aliphatic hydrocarbon is n-butane.

7. A process for the preparation of maleic anhydride which comprises subjecting an aliphatic hydrocarbon having four or more carbon atoms to gas phase oxidation reaction in the presence of a catalyst in a fluidized bed reactor, wherein the feed flow rate of oxygen-containing gas, the feed flow rate of hydrocarbon, the reaction temperature, the temperature of reaction product gas, the reaction pressure or the amount of catalyst is adjusted such that supposing that the function of reaction product gas composition is $F_L$ and the function of temperature and pressure of reaction product gas is $F_R$, the safety index F satisfies the following relationship (1):

$$F=F_L-F_R>0 \tag{1}$$

wherein $F_L$ represents the value calculated by the following equation (2):

$$F_L=C/C_T/C_O \tag{2}$$

wherein

C represents the concentration (vol %) of flammable gas in the reaction product gas, supposing that various flammable gases in the reaction product gas are numbered, 1, 2, 3, . . . , i, . . . n, respectively, and the concentration (vol %) of various flammable gases are C1, C2, C3, . . . , Ci, . . . , Cn, respectively, C can be calculated from the equation $$C = \sum_{i=1}^{n} Ci;$$

$C_O$ represents the oxygen gas concentration (vol %) in the atmosphere meaning the concentration of oxygen gas in the gas obtained by removing flammable gas from all the gases, which can be calculated from the equation $C_O$={Concentration (vol %) of oxygen in the reaction product gas/(100-$C$)}×100; and $C_T$ represents the stoichiometric flammable gas concentration (vol %) meaning the concentration of flammable component at which flammable gases in the reaction gas can be completely combusted with oxygen contained in the reaction product gas, supposing that the ratio of the stoichiometric amounts of oxygen to the amounts of each flammable component required for complete combustion are R1, R2, R3, . . . Ri, . . . , Rn, respectively, $C_T$ can be calculated from the following equation:

$$C_T = 100 \bigg/ \left[1 + \left\{\left(\sum_{i=1}^{n}(Ri \times Ci) \bigg/ \sum_{i=1}^{n} Ci\right) \bigg/ Co\right\} \times 100\right]$$

and $F_R$ represents the value calculated by the following equation (3)

$$F_R = 2.319 \times 10^{-5} \times T^2 - 1.688 \times 10^{-2} \times T + 3.288 + (P - 0.15) \times 0.3 \quad (3)$$

wherein

T represents the temperature (°C.) of reaction product gas; and P represents the reaction pressure (MpaG).

* * * * *